United States Patent [19]

Hoary

[11] 4,432,351
[45] Feb. 21, 1984

[54] VAGINAL SPECULUM

[75] Inventor: Marto J. Hoary, Eyrecourt, Ireland

[73] Assignee: Institute for Industrial Research and Standards, Dublin, Ireland

[21] Appl. No.: 274,317

[22] Filed: Jun. 16, 1981

[30] Foreign Application Priority Data

Jun. 26, 1980 [IE] Ireland .................................. 1324/80

[51] Int. Cl.³ .............................................. A61B 1/32
[52] U.S. Cl. ........................................ 128/17; 128/3; 128/20
[58] Field of Search .................... 128/12, 17, 20, 3, 18

[56] References Cited

U.S. PATENT DOCUMENTS

| 151,228 | 5/1874 | Knaffl | 128/20 |
|---|---|---|---|
| 1,020,281 | 3/1912 | Hall | 128/17 |
| 3,568,665 | 3/1971 | Lindgren et al. | 128/17 |
| 3,575,163 | 4/1971 | Gaspar | 128/17 |
| 3,702,606 | 11/1972 | Barnard | 128/17 |
| 3,752,149 | 8/1973 | Ungar et al. | 128/12 |
| 3,841,318 | 10/1974 | Olson | 128/20 |
| 4,206,750 | 6/1980 | Kaivola | 128/17 |

FOREIGN PATENT DOCUMENTS 2444450  8/1980  France .................................. 128/17

Primary Examiner—George F. Lesmes
Assistant Examiner—Nancy A. B. Swisher
Attorney, Agent, or Firm—Scully, Scott, Murphy & Presser

[57] ABSTRACT

A vaginal speculum comprising an introitus engaging ring member and a pair of vagina engaging members of arcuate shape slidable through the ring member. The introitus engaging ring member is inserted into the introitus and the vagina engaging members are moved through the ring member in the direction of the arrow A. As the vagina engaging members are moved through the ring member into the vagina, ends move apart, thereby dilating the interior of the vagina.

In another embodiment of the invention the vagina engaging members are pivotally connected to the introitus engaging ring member.

8 Claims, 8 Drawing Figures

VAGINAL SPECULUM

BACKGROUND TO THE INVENTION

1. Field of the Invention

The present invention relates to a vaginal speculum of the type comprising a pair of elongated vagina engaging members movable apart relative to each other and adapted to extend into the vagina.

2. Description of the Prior Art

Such vaginal specula are well known. In general, they are referred to as the self retaining type, in other words, they can be inserted into the vagina, and when the vagina engaging members are moved apart to dilate the vagina to the desired amount, the vagina engaging members may be locked in position. In general, these specula are used on conscious subjects. However, they may also, if desired, be used on unconscious subjects.

A particular type of vagina speculum in common general use comprises a pair of vagina engaging members pivoted together at one end. Cranked handles extend sidewardly from the vagina engaging members beyond the pivot point to substantially overlap each other. In general a screw member extends from one handle to slidably engage a hole in the other handle. Rotation of a nut on the screw member moves the handles towards and away from each other to operate the vagina engaging members. When the vagina engaging members have been adjusted to achieve the desired dilation of the vagina, the nut is then locked on the screw member.

There are a number of problems associated with these known vaginal specula. Firstly, because of the construction of the speculum, it is impossible to insert the vagina engaging members into the vagina so that the pivot point is adjacent the introitus of the vagina. The pivot point must always be outside the vagina and is usually about 2 cm from the introitus. Thus, as the members are moved apart to dilate the interior of the vagina, the introitus is dilated a proportional amount. In other words, the amount to which the introitus is dilated is a function of the distance the vagina engaging members are moved apart. It will be appreciated that this causes considerable problems in the operation of the speculum. The introitus is a particularly sensitive part of the vagina, and while it is distensible, excessive dilation of the introitus causes considerable discomfort and pain to the subject.

Secondly, since in these known vaginal specula, it is necessary to pivot the vagina engaging members together while still in position in the vagina in order to extract the speculum, in many cases, the tips of the two members nip the cervix. Additionally, because the fornix of the vagina tends to be in folds when not dilated, as the vagina engaging members are moved together, the fornix may also be nipped by the members. Needless to say, this is undesirable and particularly dangerous in pregnant subjects.

Thirdly, because the handles of these devices are operated by rotating the nut along the screw member, this operation tends to be noisy, and in many cases tends to distress the subject.

Fourthly, while these known specula can be autoclaved, because of the construction of the devices, particularly around the pivot mechanism, it is impossible to remove the stains in secluded areas around the pivot connection. This, needless to say, is objectionable.

OBJECTS OF THE INVENTION

One object of the invention is to provide a vaginal speculum which does not excessively dilate the introitus.

Another object of the invention is to provide a vaginal speculum whereby the amount by which the introitus is dilated is independent of the distance which the vagina engaging members are moved apart.

It is also an object of the invention to provide a vaginal speculum which avoids nipping the cervix when the vagina engaging members are being removed. Needless to say, another object is to avoid nipping the fornix of the vagina when the vagina engaging members are being removed.

A further object of the invention is to provide a vaginal speculum which can be operated with a relatively low noise level.

A still further object of the invention is to provide a vaginal speculum in which the component parts can easily be cleaned to remove staining and can be auto claved.

SUMMARY OF THE INVENTION

According to the invention there is provided a vaginal speculum comprising:
- an introitus engaging ring member, and
- a pair of vagina engaging members extending from the introitus engaging ring member to engage the interior of the vagina, the vagina engaging members being movable apart relative to each other to dilate the vagina.

Preferably the introitus engaging ring member is of substantially circular cross-section and adapted to extend partly into the vagina.

In another embodiment of the invention the vagina engaging members are slidable through the introitus engaging ring member into the vagina.

Preferably, at least one of the vagina engaging members is of arcuate shape.

Advantageously, both vagina engaging members are of arcuate shape.

In a further embodiment of the invention the vagina engaging members are adapted to slide together through the introitus engaging ring member.

Advantageously, portions of the vagina engaging members as they pass through the introitus engaging ring member abut each other along abutting surfaces adjacent corresponding longitudinal side edges the said portions of the vagina engaging members together forming an opening for inspection of the vagina.

Advantageously, each abutting surface of the vagina engaging members is provided with a friction surface to cause the vagina engaging members to move together through the introitus engaging ring member.

In another embodiment of the invention the vagina engaging members are of substantially semi-circular cross-section.

Alternatively, at least one of the vagina engaging members is pivotally connected to the introitus engaging ring member and means to move the vagina engaging members apart being provided.

Advantageously, both vagina engaging members are pivotally connected to the introitus engaging ring member.

Preferably, the means to move the vagina engaging members apart is provided by a pivotal member, the pivotal member being pivotal on the inner surface of one of the vagina engaging members and extending therefrom to engage the inner surface of the other vagina engaging member.

ADVANTAGES OF THE INVENTION

One advantage of the invention is that the vaginal speculum does not excessively dilate the introitus. In fact, the introitus is only dilated sufficiently to accommodate the introitus engaging ring member.

Another advantage of the invention is that because the introitus is engaged only by the introitus engaging ring member, the amount by which the introitus is dilated is totally independent of the distance the vagina engaging members are moved apart in order to dilate the interior of the vagina.

Because the vagina engaging members are of arcuate shape, the amount by which the interior of the vagina is dilated is dependent on the distance into the vagina the vagina engaging members are inserted. Conversely, on removal of the vagina engaging members, the end tips of these members inside the vagina do not come together until the tips are passing through the introitus engaging ring member. Accordingly, there is no danger of the cervix being nipped during extraction of the speculum from the vagina. Similarly, because the longitudinal side edges of the vagina engaging members only move together as the members are passing through the introitus engaging ring member, there is virtually no danger of the fornix of the vagina being nipped between the vagina engaging members on extraction of these members. Furthermore, because the longitudinal side edges of the vagina engaging members are radiused this further reduces the danger of the fornix of the vagina being nipped.

Additionally, because to dilate the vagina it is only necessary to move the vagina engaging members into the vagina, the operation of the speculum is virtually silent. In the case of the embodiment of the invention in which the vagina engaging members are pivotal on the introitus engaging ring member, the operation of this member is also virtually silent since to move the vagina engaging members apart it is merely necessary to operate the operating lever.

A still further advantage of the invention is that because the vagina engaging members and the introitus engaging ring member are separable staining can readily easily be removed from the members and they can be auto-claved where desired.

These and other object and advantages of the invention will be readily apparent from the following description of some preferred embodiments of the invention which are given by way of example only with reference to the accompanying drawings.

DETAILED DESCRIPTION OF THE INVENTION

Figure 1:
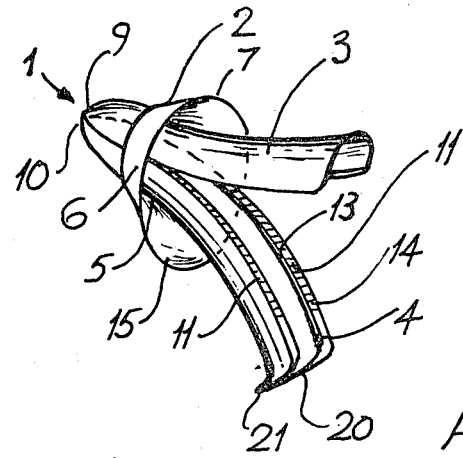
FIG. 1 is a perspective view of a vaginal speculum according to the invention.

Referring to the drawings and initially to FIGS. 1 to 6 thereof there is provided a vaginal speculum according to the invention indicated generally by the reference numeral 1. The vaginal speculum 1 comprises an introitus engaging ring member 2 and a pair of vagina engaging members 3 and 4 which are slidable through an opening 5 in the ring member 2 in the direction of the arrow A to extend into the vagina. The ring member 2 of substantially circular cross-section is of polypropylene material, but needless to say, could be of any suitable material.

Figure 2:
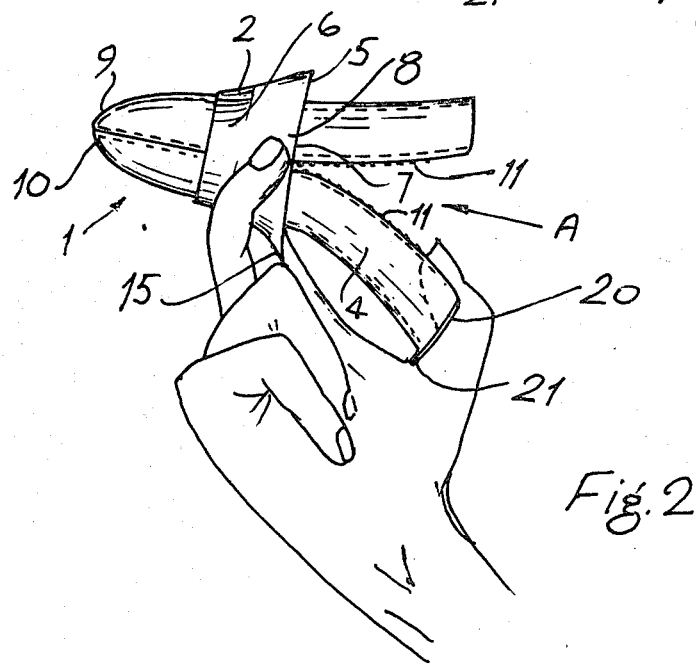
FIG. 2 is a side view of the vaginal speculum of FIG. 1.

An outer surface 6 of the ring member 2 is of such dimensions that the ring member 2 may be inserted in the introitus and extend partly into the vagina without excessively dilating the introitus. In this embodiment of the invention the outer diameter of the ring member 2 is 40 mm. On each side of the ring member 2 shallow recesses 8 are provided so that the ring member 2, in use, can be gripped between the index and second finger as illustrated in FIG. 2, or any two fingers. A radial flange 7 with a lower dished portion 15 is provided on the ring member 2. This further facilitates gripping of the speculum and assists in positive location of the ring member 2 in the introitus.

Figure 3:
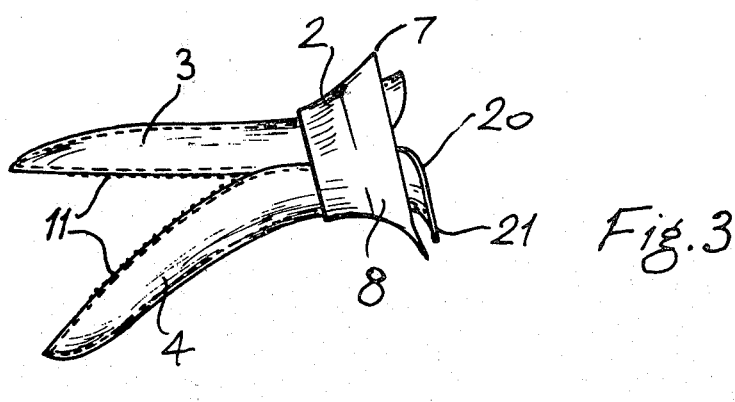
FIG. 3 is a view similar to FIG. 2 of the vaginal speculum of FIG. 1 showing the vagina engaging members in a different position.
Figure 4:
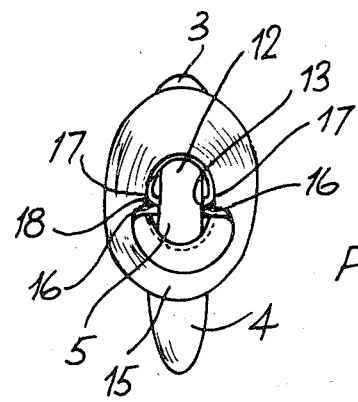
FIG. 4 is an end view of the vaginal speculum of FIG. 1.
Figure 5:
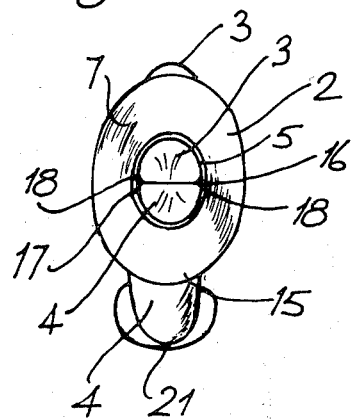
FIG. 5 is a front view of the vaginal speculum of FIG. 1.
Figure 6:
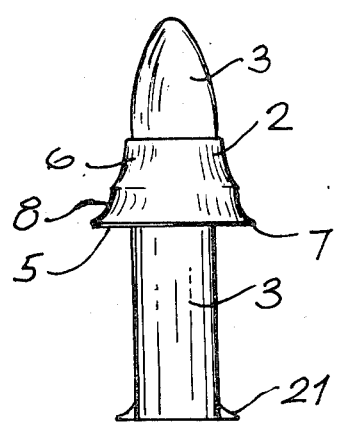
FIG. 6 is a plan view of the vaginal speculum of FIG. 1.

The vagina engaging members 3 and 4 are of light conducting and transmitting polystyrene material to facilitate illumination of the interior of the vagina. Each of the members are of arcuate shape so that as the members 3 and 4 are moved in the direction of the arrow A through the ring member 2, ends 9 and 10 of these members diverge as shown in FIG. 3 to dilate the vagina. The radius of curvature of the member 4 is substantially less than that of the member 3. This facilitates comfort for the subject. The ends 9 and 10 are tapered to provide a tapered lead-in into the vagina to facilitate comfort of the subject. The member 3 is adapted to engage the anterior fornix of the vagina while the member 4 is adapted to engage the posterior fornix. It will be appreciated that the member 3 with the greater radius of curvative when abutting the anterior fornix will cause virtually no discomfort to the bladder region of the subject, while most of the dilation of the vagina will be achieved by the member 4 in the direction of the posterior fornix of the vagina.

The vagina engaging members 3 and 4 are of substantially semi-circular cross-section and abut each other as they pass through the ring member 2 along abutting surfaces 11 to form an opening 12 through which the vagina can be inspected. Longitudinal edges 13 of each members 3 and 4 are inwardly directed to form the abutting surfaces 11. In order that the two vagina engaging members 3 and 4 move together through the ring member 2 the abutting surfaces 11 are provided with a friction surface. In this embodiment of the invention the friction surface is formed by a plurality of transverse grooves 14 of approximately half milimeter deep with a pitch of one mm. It will be appreciated that the grooves on one member co-operate with complimentary projections on the other member and vice versa. This can most clearly be seen in FIG. 1. Accordingly, movement of one of the members 3 or 4 causes corresponding movement of the other member. Needless to say, other forms of friction surfaces could be used, for example, the abutting surfaces 11 could be made tacky or by magnetic attraction.

The inwardly projecting edges 13 are radiused at 16 to avoid nipping of the fornix of the vagina adjacent to the ring member 2 as the members 3 and 4 are being withdrawn.

Longitudinal side portions of the vagina engaging members 3 and 4 are slightly flattened at 17 to co-operate with corresponding flattened surfaces 18 on the interior of the ring member 2 to avoid rotation of the members 3 and 4 in the ring member 2.

A thumb grip 20 is provided on the external end of the vagina engaging member 4 to engage the thumb of the operator. A return 21 adjacent the thumb grip 20 acts as a stop member against the ring member 2 when the members 3 and 4 are fully inserted into the vagina. It will be noted that the return 21 is of relatively large area. This facilitates collection of light for conduction through the member 4 into the vagina of the subject.

In use, the vaginal speculum 1 is picked up and inserted between the index and second finger of the operator's hand so that each finger engages one of the shallow grooves 8 as illustrated in FIG. 2. The thumb engages the thumb grip 20, and the speculum with the vaginal engaging members 3 and 4 in the position illustrated in FIG. 2 is inserted into the vagina so that the outer surface 6 of the ring member 2 engages the introitus of the vagina. The members 3 and 4 are moved in the direction of the arrow A into the vagina by the thumb bearing on the thumb grip 20. As the members 3 and 4 move into the vagina the ends 9 and 10 move apart as illustrated in FIG. 3 thereby dilating the interior of the vagina. The vagina and cervix and any other internal organs within the vagina may then be inspected through the opening 12.

To remove the speculum from the vagina the members 3 and 4 are withdrawn in the direction of the arrow B through the ring member 2 until they are in the position illustrated in FIG. 2 at which stage the ring member 2 together with the members 3 and 4 are withdrawn from the vagina. This avoids nipping of the cervix and also the fornix of the vagina.

Figure 7:
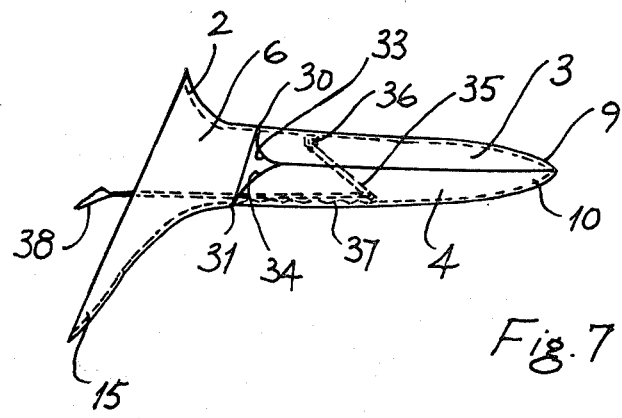
FIG. 7 is a side view of a vaginal speculum according to another embodiment of the invention.
Figure 8:
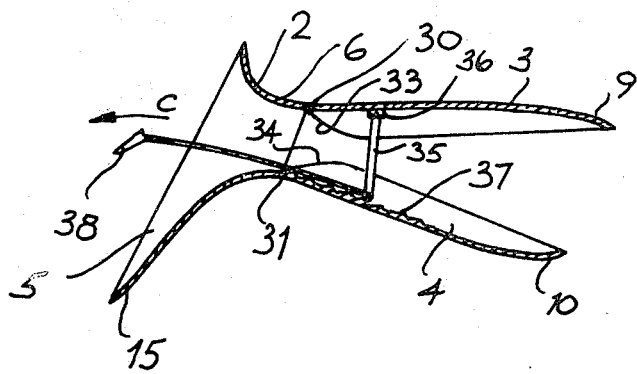
FIG. 8 is a sectional side view of the speculum of FIG. 7 showing the vagina engaging members in a different position.

Referring now to FIGS. 7 and 8 there is provided a vaginal speculum according to another embodiment of the invention. Components performing the same function as those described in the speculum with reference to FIGS. 1 to 6 are identified by the same reference numeral. In this embodiment of the invention the vagina engaging members 3 and 4 are pivotally connected to the introitus engaging ring member 2 at 30 and 31. The ring member 2 and vagina engaging members 3 and 4 are of polypropylene material injection moulded in one shot. The pivots 30 and 31 are formed by integral hinges, in other words by a weakened section of the polypropylene material. The vagina engaging members 3 and 4 in this case are straight along their longitudinal axis and are of substantially semi-circular cross-section. The ends 9 and 10 of each member 3 and 4 are tapered to provide a tapered lead-in to the vagina for comfort of the subject. Ends 33 and 34 of the members 3 and 4 are relieved to avoid nipping of the fornix when the members 3 and 4 are being moved together on extraction of the speculum from the vagina.

Means to move the vagina engaging members 3 and 4 apart to dilate the interior of the vagina is provided by a pivotal member in this case, a pivotal ring 35 pivotally connected to the inner surface of the vagnia engaging member 3 by a pivot mounting 36. The pivotal ring 35 extends from the member 3 to engage a series of indentations 37 on the inner surface of the vagina engaging member 4. It will be appreciated that the indentations 37 retain the pivotal ring 35 in position when the vagina has been dilated to the desired amount. An operating lever 38 connected to the pivotal ring 35 extends through the ring member 2 for operation of the pivotal ring 35.

It is envisaged that portions from the tips of the ends 9 and 10 may be removed from the members 3 and 4 to avoid possible nipping of the cervix when the members 3 and 4 are being moved together for extraction of the speculum.

In use, this vagina speculum is inserted into the vagina with the introitus engaging ring member in the introitus. The lever 38 is then moved in the direction of the arrow C until the vagina engaging members 3 and 4 have dilated the vagina to the desired position. The pivotal ring 35 engages an indentation 37 to retain the members 3 and 4 in the desired position. The internal organs of the vagina can then be inspected through the opening 5 in the ring member 2. To remove the vaginal speculum from the vagina the lever 38 is moved inwardly through the ring 2 and the members 3 and 4 move together and the speculum may then be removed from the vagina.

Similarly, as in the case of the vaginal speculum described with reference to FIGS. 1 to 6 light will be transmitted and conducted through the material of this speculum to illuminate the interior of the vagina for examination.

Needless to say, although in the case of the embodiment of the invention described with reference to FIGS. 7 and 8 both vagina engaging members are pivotally connected to the introitus engaging ring member, it is envisaged that only one vagina engaging member need be pivotal, the other member and preferably the member adapted to abut the anterior fornix could be rigidly connected to the introitus engaging ring member.

It is also envisaged that the vaginal specula just described could be manufactured from a re-usable material, in other words, from a material which lends itself to cleaning and sterilising by, for example, auto claving. In which case it is envisaged that the materials used in the components of the specula would by polysulphone. Although, needless to say, any other suitable material could be used whether plastics or metal. Preferably, the materials used should have a low co-efficient of thermal conductivity in order to avoid discomfort to the subject.

Indeed, in the case of the vaginal speculum described with reference to FIGS. 1 to 6 it is envisaged that the ring member 2 may be manufactured from a sterilisable material, for example, stainless steel or a sterilisable plastics material and the vagina engaging members 3 and 4 could be manufactured from a disposable plastics material or indeed glass.

It will be appreciated, that although both of the vagina engaging members of the speculum described with reference to FIGS. 1 to 6 have been described as being of arcuate shape, this is not necessary, in fact, both members could be straight if desired. Although, it will be appreciated that to achieve all the advantages of the invention it is preferable that at least one of the members should be of arcuate shape. Neither, is it necessary for the arcuate members to have different radii of arc. Furthermore, it will be appreciated that it is not necessary for the vagina engaging member to be adapted to move together through the ring member they could move independently of each other. And for this reason it will be appreciated that it is not necessary that the members should abut each other on passing through the ring member.

Indeed, although the vagina engaging members of both embodiments of the specula just described have been described as being of semi-circular cross-section it will be appreciated that these members could have been of any suitable cross-section, similarly it will be appreciated that the introitus engaging ring member could be of any other suitable cross-section. Indeed, in the case of the embodiment described with reference to FIGS. 1 to 6, it is envisaged that depending on the cross-section of the vagina engaging members, these members could abut together along any suitable portion as they passed through the ring member.

Furthermore, it is envisaged that in the case of the embodiment of the invention described with reference to FIGS. 1 to 6, the inner surface of the introitus engaging ring member could be convex along its longitudinal axis, to provide a neck of reduced cross-section intermediate the ends of the ring member. This, it will be appreciated would cause the ends of the vagina engaging members, where the vagina engaging members be straight or of arcuate shape, to move apart as the members are inserted through the ring member.

Indeed, it is envisaged that a co-operating tract and groove may be provided on the interior surface of the ring member and the exterior surfaces of the vagina engaging members to facilitate operation of the speculum.

Needless to say, it will be appreciated that it is not necessary for the ring members of either embodiments of the specula just described to have a flange.

Furthermore, it will be appreciated that it is not necessary for the materials of the specula to be light transmitting or light conductive.

In the case of the embodiment of FIGS. 1 to 6 it is envisaged that in order to prevent the members 3 and 4 of the speculum rotating in the ring member 2, inwardly projecting dimples could be provided on the interior surface of the ring member 2 to engage between the radiused portions 16 of the members 3 and 4.

Regarding the embodiment of the invention described with reference to FIGS. 7 and 8 although it has not been described, it is envisaged that the longitudinal edges of the members 3 and 4 could be provided with radii similar to the radii 16 of the members 3 and 6 of the speculum of FIGS. 1 to 6 to avoid nipping of the fornix of the vagina.

It is further envisaged that the vagina engaging members may be provided with a stop means to prevent them from being withdrawn completely from the ring member. Such a stop means could be provided by an outwardly projecting dimple on the vagina engaging members which would engage the ring member. Alternatively, the stop means could be provided by slightly increasing the cross sectional area of the vagina engaging members at the position where it is desired to limit the stroke of the members. Such an increase in cross-section would prevent the vagina engaging members passing further through the ring member. Needless to say, by suitably sizing the stop means it would be possible to completely withdraw the vagina engaging members from the ring member by applying additional force.

It is also envisaged that one of the vagina engaging members could be adapted to move faster through the ring member than the other. This, it will be appreciated could be achieved by suitable gearing between the members.

I claim:
1. A vaginal speculum comprising:
   an introitus engaging ring member having a longitudinally extending outer surface to project partly into the introitus, and
   a pair of elongated vagina engaging members slideable longitudinally through the introitus engaging ring member to engage the interior of the vagina, at least one of the vagina engaging members being of arcuate shape in longitudinal cross-section over at least a portion of its length so that on sliding longitudinally through the ring member the vagina engaging members move apart relative to one another to engage the vagina.
2. A vaginal speculum as claimed in claim 1 in which the introitus engaging ring member is substantially circular in transverse cross-section.
3. A vaginal speculum as claimed in claim 1 in which both the vagina engaging members are of arcuate shape in longitudinal cross-section.
4. A vaginal speculum as claimed in claim 3 in which the radius of curvature of the vagina engaging member which in use engages the posterior fornix of the vagina is less than the radius of curvature of the vagina member which in use engages the anterior fornix of the vagina.
5. A vaginal speculum as claimed in claim 1 in which the vagina engaging members are adapted to slide together through the introitus engaging ring member.
6. A vaginal speculum as claimed in claim 5 in which portions of the vagina engaging members as they pass through the introitus engaging ring member abut each other along abutting surfaces adjacent corresponding longitudinal side edges, the said portions of the vagina engaging members together forming an opening for inspection of the vagina.
7. A vaginal speculum as claimed in claim 6 in which each abutting surface of the vagina engaging members is provided with a friction surface to cause the vagina engaging member to move together through the introitus engaging ring member.
8. A vagina engaging speculum as claimed in claim 6 in which the vagina engaging members are substantially semi-circular in transverse cross-section.

* * * * *